US009617881B2

(12) United States Patent
Wirth et al.

(10) Patent No.: US 9,617,881 B2
(45) Date of Patent: Apr. 11, 2017

(54) ACTUATOR ARRANGEMENT ON A VEHICLE STRUCTURE

(71) Applicant: Eberspächer Exhaust Technology GmbH & Co. KG, Neunkirchen (DE)

(72) Inventors: Georg Wirth, Kirchheim/Teck (DE); Michael Bott, Holzkirchen (DE)

(73) Assignee: Eberspächer Exhaust Technology GmbH & Co. KG, Neunkirchen (DE)

( * ) Notice: Subject to any disclaimer, the term of this patent is extended or adjusted under 35 U.S.C. 154(b) by 135 days.

(21) Appl. No.: 14/532,199

(22) Filed: Nov. 4, 2014

(65) Prior Publication Data

US 2015/0124990 A1 May 7, 2015

(30) Foreign Application Priority Data

Nov. 6, 2013 (DE) ........................ 10 2013 222 548

(51) Int. Cl.

| | |
|---|---|
| ***A61F 11/06*** | (2006.01) |
| ***G10K 11/16*** | (2006.01) |
| ***H03B 29/00*** | (2006.01) |
| ***F01N 1/06*** | (2006.01) |
| ***G10K 11/00*** | (2006.01) |
| ***G10K 11/178*** | (2006.01) |
| *F01N 13/18* | (2010.01) |

(52) U.S. Cl.

CPC .......... *F01N 1/065* (2013.01); *F01N 13/1811* (2013.01); *F01N 13/1822* (2013.01); *G10K 11/004* (2013.01); *G10K 11/1788* (2013.01); *F01N 13/1805* (2013.01); *F01N 13/1855* (2013.01); *G10K 2210/12822* (2013.01)

(58) Field of Classification Search

CPC ............ G10K 11/1788; G10K 11/004; G10K 2210/12822; F01N 13/1811; F01N 13/1822; F01N 1/065; F01N 13/1805; F01N 13/1855

USPC ........................................................ 381/71.5

See application file for complete search history.

(56) References Cited

U.S. PATENT DOCUMENTS 6,005,957 A 12/1999 Meeks
2002/0047074 A1* 4/2002 Vanderveen ......... F02M 35/021 248/200

FOREIGN PATENT DOCUMENTS

GB 2 461 284 A 12/2009
JP H09112242 A 4/1997

* cited by examiner

*Primary Examiner* — Paul S Kim
(74) *Attorney, Agent, or Firm* — McGlew and Tuttle, P.C.

(57) ABSTRACT

An arrangement (1) of an electroacoustic actuator (2) on a vehicle structure (3) of a motor vehicle, has a housing (4), in which at least one loudspeaker (7) is arranged, which separates a front volume (8) from a rear volume (9) in the housing (4). The actuator (2) has a sound emission pipe (5), which projects outwards from the housing (4) and which is fluidically coupled with the front volume (8). A reduced introduction of noise into the vehicle arises when the actuator (2) is held on the vehicle structure (3) with a plurality of holding devices (19), which are arranged on the housing (4) in a circumferential direction (20) of the housing (4) spaced apart from one another. Each holding device (19) is designed as springy in a holding direction (21) and as rigid transversely thereto.

20 Claims, 4 Drawing Sheets

ACTUATOR ARRANGEMENT ON A VEHICLE STRUCTURE

CROSS REFERENCE TO RELATED APPLICATIONS

This application claims the benefit of priority under 35 U.S.C. §119 of German Patent Application DE 10 2013 222 548.2 filed Nov. 6, 2013, the entire contents of which are incorporated herein by reference.

FIELD OF THE INVENTION

The present invention pertains to an arrangement of an electroacoustic actuator on a vehicle structure of a motor vehicle.

BACKGROUND OF THE INVENTION

An electroacoustic actuator usually comprises a housing, in which is arranged at least one loudspeaker, which separates a front volume from a rear volume in the housing. Further, the actuator may have a sound emission pipe, which protrudes outwards from the housing and which is fluidically coupled with the front volume.

Such an electroacoustic actuator may be used in an exhaust system as an active muffler in order to reduce disturbing amplitudes in the noises transported in the exhaust system by means of active noise control. Further, such an actuator may also be used to specifically generate or reinforce certain frequencies in order to operate a so-called sound design. Mixed applications are also conceivable, in which the respective actuator muffles or reduces disturbing frequencies by means of active noise control, while it generates or reinforces desired frequencies at the same time.

For the use of such an actuator, it is basically possible to fix the sound emission pipe directly on an exhaust pipe of the exhaust system in order to be able to introduce the sound waves generated by means of the actuator directly into the exhaust gas stream. Further, the actuator can be springily connected with a vehicle structure via its housing, such that the actuator can vibrate in relation to the vehicle structure together with the exhaust system. Because of confined installation situations, it is frequently not possible to fix the actuator directly to the exhaust system via the sound emission pipe. In these cases, it is basically possible to fix the actuator overall to the vehicle structure and to arrange the sound emission pipe detached in the surrounding area. As an alternative, it is also conceivable to connect the sound emission pipe with an exhaust pipe via a springy connection piece in order to be able to arrange the housing of the actuator at a different, more suitable site.

In the cases, in which the housing does not have a rigid or inflexible coupling with the exhaust pipe via the sound emission pipe, there is the risk that the housing is offset in vibrations during the operation of the actuator. In a rigid connection of the housing to the vehicle structure, the vehicle structure may consequently also be excited locally to vibrate, which may lead to an undesired development of noise in the vehicle. The vibration excitation of the housing can be attributed to the fact that the loudspeaker with its cage is ultimately supported on the housing. The cage stretches a diaphragm of the loudspeaker, on the one hand, and, on the other hand, carries an electromagnetic driver, which is drive-connected with the diaphragm. Each vibration introduced into the diaphragm by the driver acts as an “action,” whose “reaction” must be supported by the driver via the cage on the housing.

SUMMARY OF THE INVENTION

An object of the present invention is to provide an improved embodiment for the arrangement of an actuator on a vehicle structure, which is characterized, in particular, by a reduced transmission of vibrations between the actuator and the vehicle structure.

According to the invention, an arrangement of an electroacoustic actuator is provided for a vehicle structure of a motor vehicle. The actuator has a housing, in which is arranged at least one loudspeaker, which separates a front (first) volume from a rear (second) volume in the housing. The actuator has a sound emission pipe, which protrudes outwards from the housing and which is fluidically coupled with the front volume. The actuator is held on the vehicle structure with a plurality of holding devices. The holding devices are arranged spaced apart from one another in a circumferential direction of the housing. The holding devices are each designed to be springy in a holding direction and to be rigid transversely thereto.

The present invention is based on the general idea of holding the actuator on the vehicle structure by means of a plurality of separate holding devices, whereby these holding devices are arranged in a circumferential direction of the housing spaced apart from one another and are distributed on the housing. Further, the holding devices are designed as springy (moveable/resilient) in a holding direction, while they are designed as rigid transversely to the holding direction. The terms “springy” and “rigid” are defined here in relation to one another, such that the respective holding device has a greater elasticity in the holding direction than transversely thereto. Likewise, the respective holding device transversely to the holding direction has a greater rigidity than parallel to the holding direction. Accordingly, the holding device may also have a certain elasticity transversely to the holding direction, which, however, turns out to be markedly smaller than parallel to the holding direction. For example, the elasticity of the respective holding device parallel to the holding direction is at least one order of magnitude greater than transversely to the holding direction.

By means of the springy holding devices in the holding direction, vibrations of the housing in the holding direction are not transmitted to the vehicle structure or only to a highly reduced extent. On the other hand, due to the rigidity of the holding directions transversely to the holding direction, a sufficient fixing of the actuator on the vehicle structure is achieved. Thus, the risk of an undesired transmission of sound conducted through solids from the actuator to the vehicle structure can be significantly reduced.

According to one advantageous embodiment, the holding directions of the individual holding directions may run parallel to one another. Consequently, the entire housing or the entire actuator essentially has only the holding direction as a degree of freedom for relative movements with regard to the vehicle structure. On the one hand, this improves the vibration-related uncoupling between the vehicle structure and the actuator parallel to the holding direction, while, on the other hand, the fixing of the actuator to the vehicle structure transversely thereto is reinforced at the same time.

According to another embodiment, the holding directions of the holding devices may run parallel to an excitation direction of the loudspeaker, in which the loudspeaker transmits excitation forces to the housing during the operation of the actuator. The excitation direction of the loudspeaker essentially corresponds to the lifting direction or vibration direction of a loudspeaker diaphragm, whereby the excitation forces counteract the forces that are necessary for deflecting the loudspeaker diaphragm, which results from the physics principle of "action equals reaction." Due to the parallel alignment of the holding directions to said excitation direction, the vibrations generated by the loudspeaker in the housing can be specifically muffled.

According to another embodiment, the respective holding device may have a bracket rigidly connected with the housing, which bracket is springily connected via a coupling means in the holding direction and rigidly with the vehicle structure transversely thereto. In order words, the respective holding device has a bracket connected rigidly or inflexibly with the housing, such that the springy suspension ultimately results via a coupling means, which acts between the respective bracket and the vehicle structure. The use of such brackets facilitates the connection of the holding devices to the housing.

According to another embodiment, the holding devices or the brackets may define a holding plane, which extends vertically to the excitation direction of the loudspeaker. Preferably, there are thus at least three holding devices in order to be able to clearly said holding plane. The housing can be securely supported on the vehicle structure by means of three or more holding devices.

The holding directions of the holding devices are preferably aligned vertically to the holding plane, such that the housing is supported torque-free with regard to vibrations.

In another embodiment, the holding devices or the brackets may be arranged equidistantly to a force inlet point of the loudspeaker, from which it transmits dynamic excitation forces to the housing from the loudspeaker during the operation of the actuator. This action also leads to the holding devices ultimately not having to support torques. The term "equidistant" is defined in the present context, such that preferably equal distances are present, but basically small deviations of maximum 10% with regard to the distances of the holding devices from the force inlet point are tolerable and can still be regarded as equidistant.

According to another embodiment, the holding devices or brackets may be arranged equidistantly to a mass center of the actuator. The result of this action is that static forces, namely the weight force of the actuator, also do not transmit torque between the actuator and the vehicle structure. Here as well, the term "equidistant" is defined, such that identical distances are desired, but deviations of maximum 10% are tolerable.

In another embodiment, provisions may be made for a mass center of the actuator and a force inlet point, from which it transmits dynamic excitation forces to the housing from the loudspeaker during the operation of the actuator, to be arranged essentially in one another or in the direction of gravity above one another. Ultimately, this action also leads to the generation of torques being reduced in the housing during the operation of the actuator.

In another embodiment, provisions may be made to arrange the loudspeaker in the housing, so that an excitation direction of the loudspeaker, in which the loudspeaker transmits excitation forces to the housing during the operation of the actuator, runs parallel to the direction of gravity. Due to this action, a resulting excitation force of the loudspeaker runs essentially through the mass center of the actuator. Since the excitation force and gravity thus run coaxially, the embodiment of a torque-free holding of the housing on the vehicle structure is simplified.

In another advantageous embodiment, provisions may be made for a coupling means of the respective holding device, which connects a bracket of the respective holding device, which is rigidly connected with the housing, with the vehicle structure, to be designed as an elastomer bearing, which is designed as springy in the holding direction and as rigid transversely thereto. The use of elastomer bearings, which have a direction-dependent elasticity, makes possible, on the one hand, a sufficient absorption of vibrations, and, on the other hand, a sufficient holding for the actuator on the vehicle structure.

According to a special variant, the elastomer bearing may have a first, especially ring-shaped, elastomer area, which supports the bracket in the holding direction on the vehicle structure, whereby the elastomer bearing has, in addition, a second, especially ring-shaped elastomer area, which supports the bracket in the holding direction on a side facing away from the vehicle structure at a disk. The disk may now be rigidly connected with the vehicle structure by means of a screw connection, which extends through the two elastomer areas and through the bracket. Such an elastomer bearing has a relatively high elasticity in the holding direction, while at the same time it has a comparatively high rigidity transversely to the holding direction.

In a variant, the screw connection may, in addition, extend through a spacer sleeve, which supports the disk in the holding direction on the vehicle structure. By means of such a spacer sleeve, high holding forces can be achieved between the elastomer bearing and the vehicle structure, whereby at the same time a predefined pretensioning for the elastomer areas can be achieved.

The two elastomer areas here may be designed as integral in a common elastomer body. Further, it is conceivable to embody the two elastomer areas by means of separate or separated elastomer bodies.

In another embodiment, said coupling means may have an elastomer body, which, on the one hand, is rigidly connected with the respective bracket, and, on the other hand, is rigidly connected with a holder fastened to the vehicle structure, whereby the elastomer body is designed as springy in the holding direction and as rigid transversely thereto. This embodiment has an especially simple and thus inexpensive design. For example, the elastomer body may be arranged in the manner of a rubber strap, in which, on the one hand, the bracket and, on the other hand, the respective holder can be attached. According to a preferred variant, the respective bracket may have a more or less wire-shaped design. In addition or as an alternative, the respective holder may also have a more or less wire-shaped design.

In another embodiment, the respective coupling means may have at least one elastomer body and/or at least one spring element as well as a linear guide, which defines the holding direction. In this case, the functions of the springy holder in the holding direction and the rigid transverse support are split between two different components of the coupling means. The springy transmission of holding forces takes place via the elastomer body or via the spring element, while the rigid transverse support takes place via the linear guide.

According to another advantageous embodiment, provisions may be made for the actuator to be held exclusively via the holding device in a vehicle structure. In particular, there is no transmission of holding forces between the sound emission pipe and the vehicle structure or an exhaust system. In addition or as an alternative, provisions may be made for the sound emission pipe to be arranged in a surrounding area of the actuator. In this case, any connection of the sound emission pipe, for example, to an exhaust system, is also absent.

Finally, the present invention thus also pertains to a vehicle, which has a vehicle structure and at least one actuator, which is arranged on the vehicle structure by means of an arrangement of the type described above.

It is apparent that the features mentioned above and those still to be explained below can be used not only in each combination indicated, but also in other combinations or alone, without going beyond the scope of the present invention.

Preferred exemplary embodiments of the present invention are shown in the drawings and are explained in detail in the following description, in which identical reference numbers refer to identical or similar or functionally identical components. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
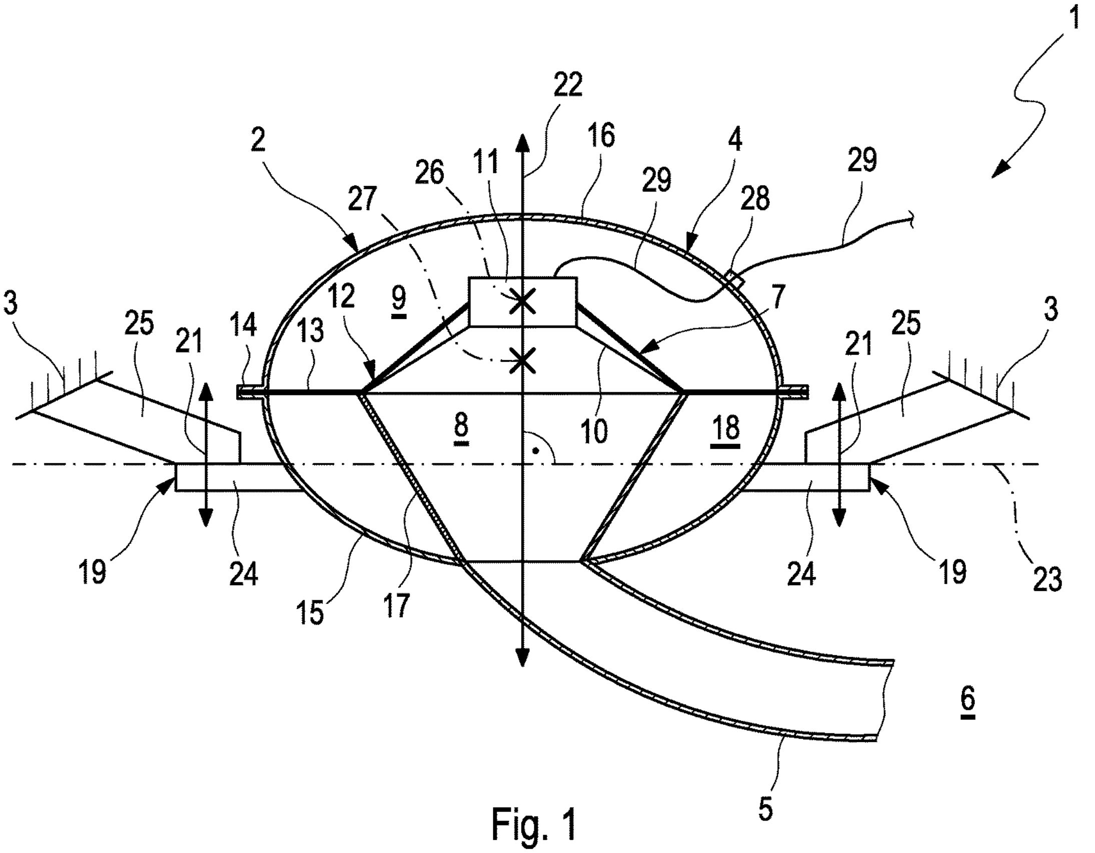
FIG. 1 is a highly simplified sectional view of an arrangement of an actuator on a vehicle structure.
Figure 2:
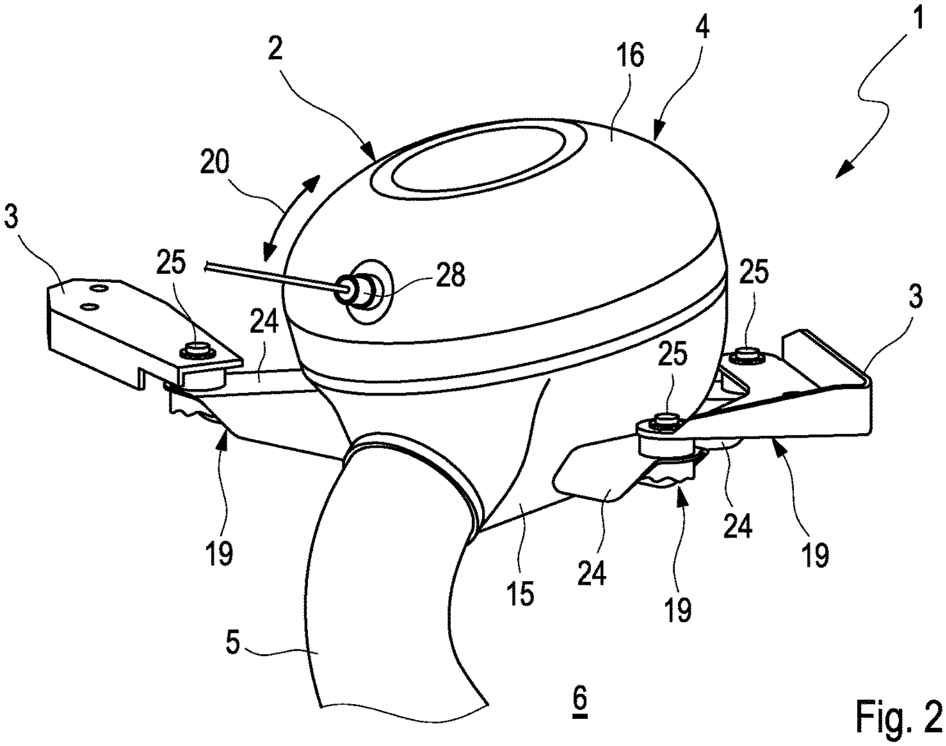
FIG. 2 is an isometric view of the arrangement.
Figure 4:
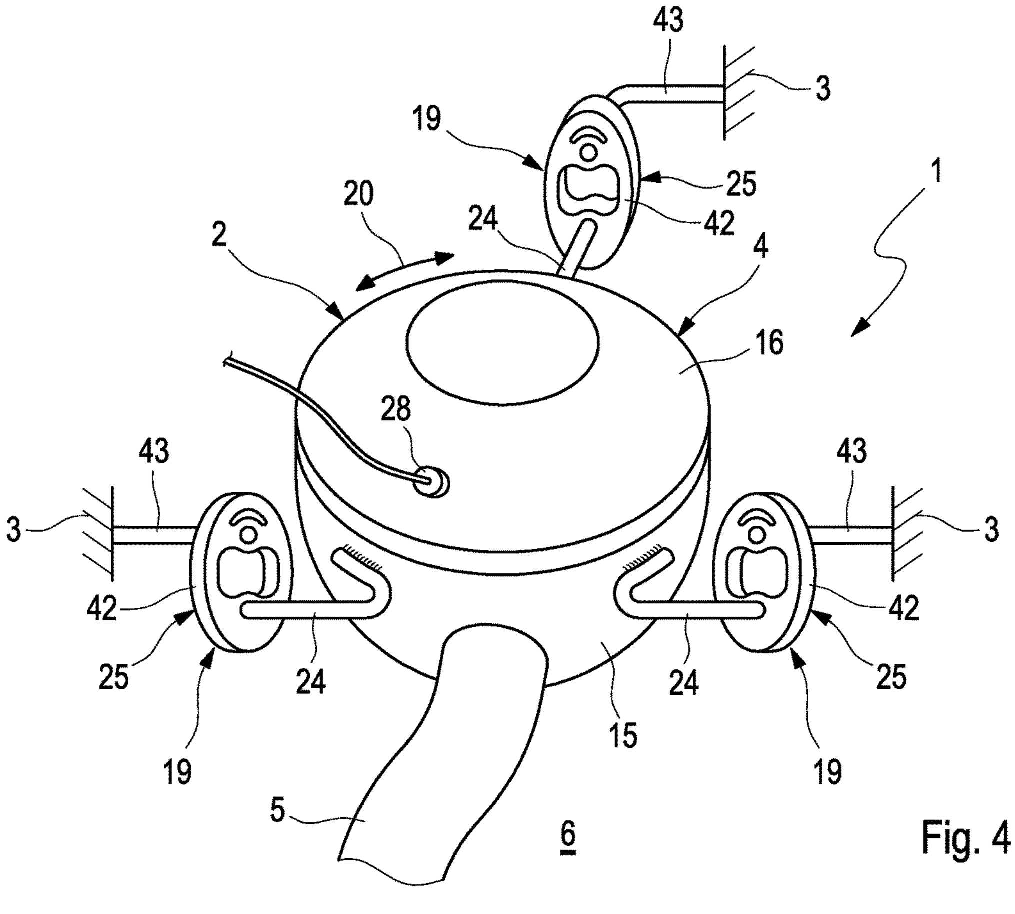
FIG. 4 is a highly simplified isometric view of the arrangement, but in a different embodiment.

Referring to the drawings in particular, FIGS. 1, 2 and 4 show each an arrangement 1 of an electroacoustic actuator 2 on a vehicle structure 3, which is shown only in a rudimentary manner or partly, of a motor vehicle, otherwise not shown. The actuator 2 has a housing 4 as well as a sound emission pipe 5, which protrudes outwards from the housing 4 into a surrounding area 6.

According to FIG. 1, at least one loudspeaker 7, which separates a front volume 8 from a rear volume 9 in the housing 4, is arranged in the housing 4. In the preferred example shown, the actuator 2 has only one loudspeaker 7. The loudspeaker 7 usually has a diaphragm 10 as well as an electromagnetic driver 11 for driving the diaphragm 10. The driver 11 and the diaphragm 10 are drive-connected in the manner shown.

Further, a cage 12 is provided, which carries the driver 11, on the one hand, and stretches the diaphragm 10, on the other hand. In addition, the cage 12 is used for fastening the loudspeaker 7 to the housing 4. For this, a conduit 13 of the cage 12 is inserted into a flange area, via which two housing shells, namely a lower housing shell 15 and an upper housing shell 16 of the housing 2, are fastened to one another. The cage 12 is permeable towards the rear volume 9, such that the rear volume 9 extends through the cage 12 up to a rear side of the diaphragm 10 facing towards the upper housing shell 16. In addition, in the embodiment shown here, a funnel 17 is arranged in the housing 4, which funnel 17 surrounds the front volume 8 and which connects a front side facing towards the front volume 8 fluidically or acoustically with the sound emission pipe. In other words, the sound emission pipe 5 is fluidically coupled with the front volume 8. In this way, sound, which is generated by means of the diaphragm 10, can be radiated via the funnel 17 into the sound emission pipe 5 and through the sound emission pipe 5 into the surrounding area 6. In the example of FIG. 1, the funnel 17 in the lower housing shell 15 separates the front volume 18, in addition, from an additional volume 18. The conduit 13 is advantageously acoustically permeable, for example, by means of corresponding perforations or openings. In this way, the additional volume 18 can be acoustically added to the rear volume, as a result of which the actuator 2 has an especially large rear volume (9+18).

The actuator 2 may be designed as an active muffler or as a sound generator or as a combination of active muffler and sound generator in order to form a sound emission of the vehicle. If the vehicle is equipped with an internal combustion engine, an emission of disturbing noise into the surrounding area of the vehicle can be reduced with the actuator 2 designed as an active muffler. In vehicles with smaller internal combustion engines and/or in vehicles with electric drive, it is, on the other hand, possible to generate a sound emission for the vehicle specifically by means of the actuator 2. Here, an acoustic feedback of the vehicle driver is important to get a feeling of the current performance of the drive in a conventional vehicle. The improved passive vehicle safety which is accompanied by a corresponding sound emission, is not insignificant exactly in electric vehicles, since the vehicle can consequently be better perceived by other road users. Because the travel noise is reduced in electric vehicles at slow vehicle speeds essentially to the rolling away noise, there is the risk that an electric vehicle is not heard by a pedestrian or bicyclist.

According to FIGS. 1, 2 and 4, the actuator 2 is held on the vehicle structure 3 by means of a plurality of holding devices 19. The holding devices 19 here are arranged distributed in a circumferential direction 20 of the housing 4 indicated by means of a double arrow in FIGS. 2 and 4, such that they are spaced apart from one another in the circumferential direction 20. A variant, in which precisely three such holding devices 19 are provided, is preferred here. Theoretically, a solution with only two holding devices 19 is also conceivable.

The holding devices 19 are each mounted on the housing 4 and preferably on the lower housing shell 15. The holding devices 19 are each designed as springy in a holding direction, indicated by means of a double arrow in FIGS. 1, 3 and 5-7, and as rigid transversely to the holding direction 21. Preferably, the holding directions 21 of all holding devices 19 run parallel to one another. Furthermore, the holding directions 21 preferably run parallel to an excitation direction 22 of the loudspeaker 7 indicated by means of a double arrow in FIG. 1. In the excitation direction 22, the loudspeaker 7 transmits excitation forces to the housing 4 during the operation of the actuator 2. Further, it can be gathered from FIG. 1 that, according to a preferred embodiment, the holding devices 19 define a holding plane 23. In other words, the holding devices 19 lie in a common holding plane 23. The holding plane 23 now extends vertically to the excitation direction 22 of the loudspeaker 7. Thus, the holding directions 21 are also vertical to the holding plane 23.

According to FIGS. 1-7, the respective holding device 19 has a bracket 24, which is rigidly connected with the housing 4, as well as a coupling means 25, by means of which the respective bracket 24 is connected springily with the vehicle structure 3 in the holding direction 21 and rigidly transversely thereto. According to FIG. 1, said brackets 24 or the holding devices 19 can now be arranged on the housing 4 equidistantly to a force inlet point 26 of the loudspeaker 7, from which it transmits dynamic excitation forces from the loudspeaker 7 to the housing 4 during the operation of the actuator 2. The force inlet point 26 is located here in the driver 11, in which the reaction forms during the excitation of the diaphragm 10 (action). These excitation forces are now transmitted from the driver 11 via the cage 12 and the conduit 13 into the housing 4.

Further, provisions are made here for the holding devices 19 or their brackets 24 to be arranged on the housing 4 equidistantly to a mass center 27 of the actuator 2. In this arrangement 1, this mass center 27 and the above-mentioned force inlet point 26 are arranged above one another in the direction of gravity. In addition, the loudspeaker 7 is preferably arranged in the housing 4, such that the excitation direction 22 runs parallel to the direction of gravity. Furthermore, the loudspeaker 7 is preferably arranged in the housing 4, such that a resulting excitation force, which passes through the force inlet point 26, additionally also passes through the mass center 27. Thus, the excitation forces and gravity act uniformly on the actuator 2, as a result of which especially a torque formation within the actuator 2 can be avoided.

In addition, an electric supply 28, by means of which an electric cable 29 can be connected through the housing 4 with the loudspeaker 7 or with the driver 11, is indicated in FIGS. 1, 2 and 4. Further, additional electrical or electronic components of the actuator 2, for example, a microphone or a temperature sensor, may also be connected via the cable 29.

Figure 3:
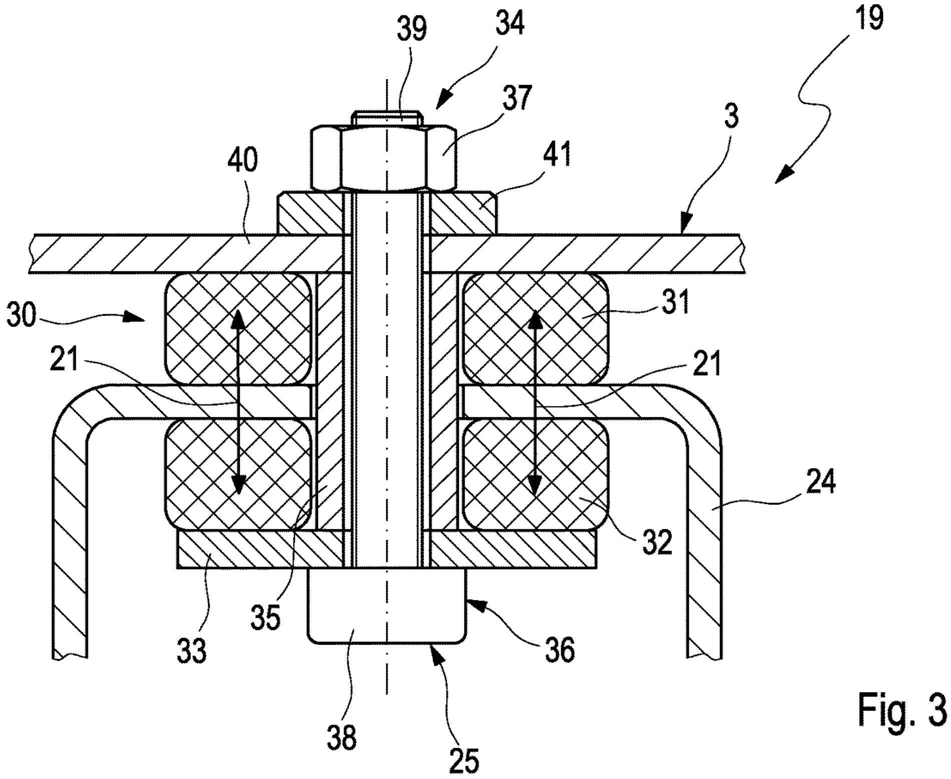
FIG. 3 is a simplified sectional view through a holding device of the arrangement from FIG. 2.
Figure 5:
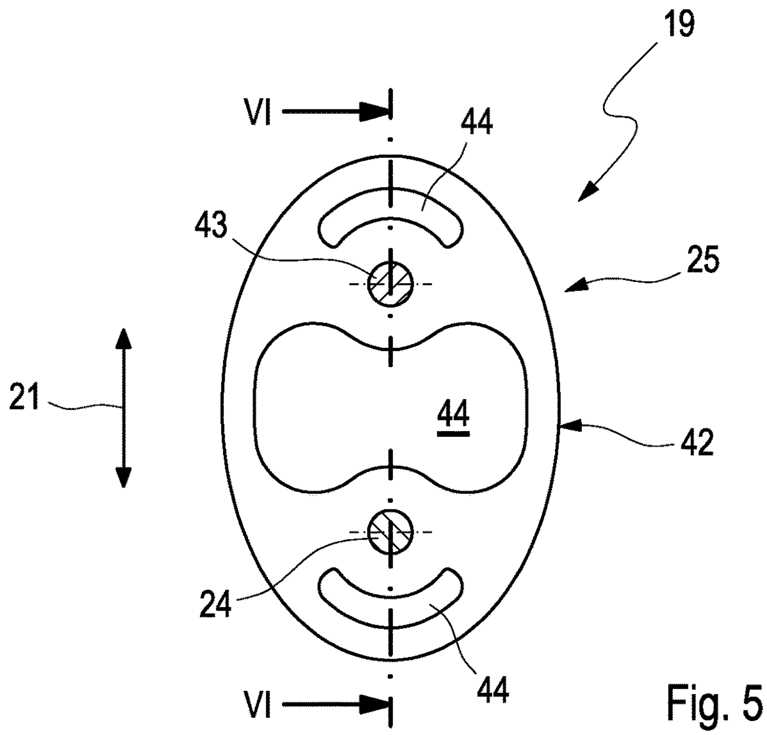
FIG. 5 is an enlarged view of a coupling means of the holding device used in FIG. 4.
Figure 6:
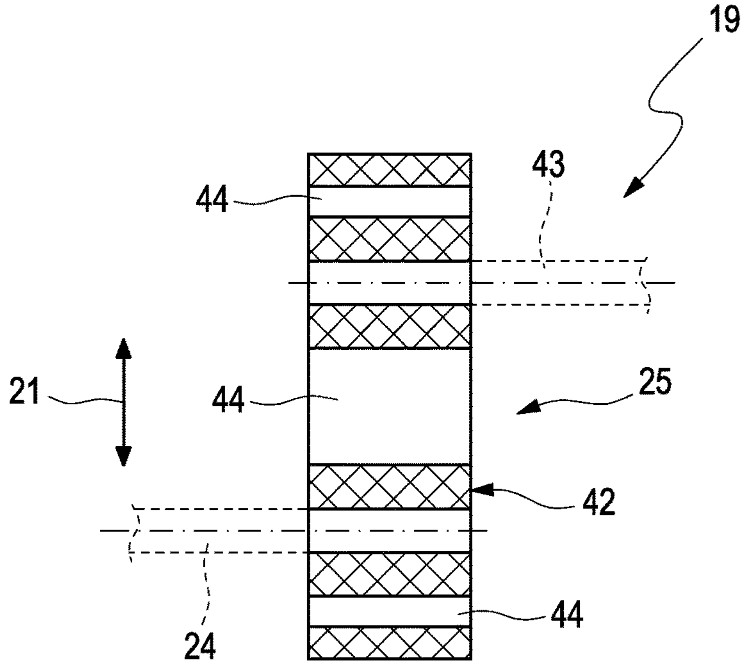
FIG. 6 is a sectional view of the coupling means according to intersecting lines VI in FIG. 5.
Figure 7:
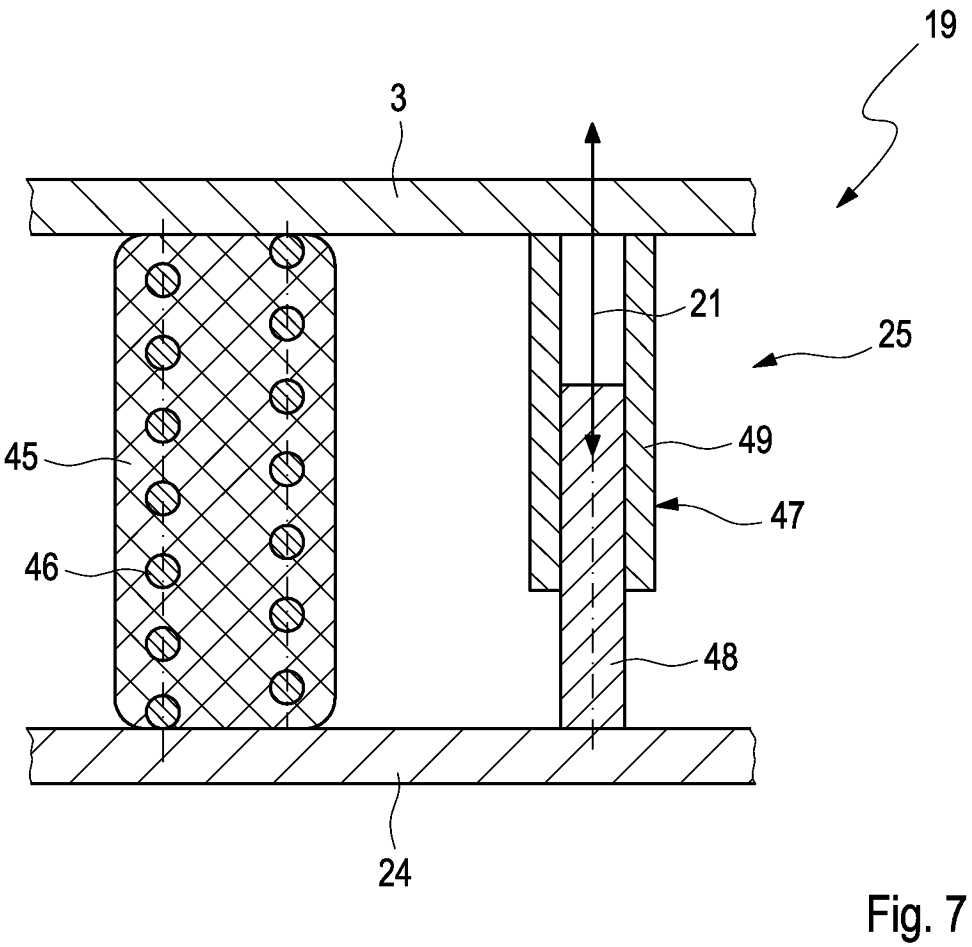
FIG. 7 is a sectional view of a holding device in another embodiment.

Special embodiments of the holding devices 19 are explained in detail below with reference to FIGS. 3-7. FIG. 3 shows a possible embodiment of the holding device 19, as it may be used in the embodiment of the arrangement 1 shown in FIG. 2. FIGS. 5 and 6 show a coupling means 25, as it is used in the holding device 19 of the embodiment shown in FIG. 4. FIG. 7 shows a holding device 19 according to another embodiment.

In the embodiment shown in FIG. 3, the coupling means 25 of the holding device 19 is designed as an elastomer bearing 30, which has a ring-shaped first elastomer area 31 and a ring-shaped second elastomer area 32. The first elastomer area 31 supports the bracket 24 in the holding direction 21 on the vehicle structure 3. The second elastomer area 32 supports the bracket 24 in the holding direction 21 on a disk 33, which is arranged on a side of the bracket 24 facing away from the vehicle structure 3. The disk 33 is rigidly connected with the vehicle structure 3 by means of a screw connection 34. To this end, the screw connection 34 extends through the two elastomer areas 31, 32 and through the bracket 24. In the example, the screw connection 34 extends, in addition, through a spacer sleeve 35, via which the disk 33 is supported in the holding direction 21 on the vehicle structure 3. The screw connection 34 has, in the example, a screw 36 as well as a nut 37. A screw head 38 of the screw 36 is supported on the disk 33. A screw shank 39 of the screw 36 extends through the disk 33, through the spacer sleeve 35 and thus through the two elastomer bodies 31 and 32 as well as through the bracket 24 and through a connection area 40 of the vehicle structure 3. The nut 37 is screwed with the screw shank 39 and is supported via a supporting disk 41 on a side facing away from the bracket 24 at the connection area 40 of the vehicle structure 3. In the example of FIG. 3, the two elastomer areas 31 and 32 are separate elastomer bodies. However, basically also conceivable is an embodiment, in which the two elastomer areas 31, 32 are formed integrally, i.e., materially uniformly on a common elastomer body. For example, the two elastomer areas 31, 32 may be connected with one another via a section likewise passed through the bracket 24.

In the embodiment shown in FIGS. 4-6, the coupling means comprises an elastomer body 42, which is configured here as a rubber strap. Here, on the one hand, the elastomer body 42 is rigidly connected with the respective bracket 24 and thus with the housing 24 via the bracket 24. On the other hand, the elastomer body 42 is rigidly connected with a holder 43, which is in turn fastened to the vehicle structure 3. To this extent, the respective elastomer body 42 is rigidly connected with the vehicle structure 3 via the respective holder 43. The respective elastomer body 42 is designed here, such that it is designed as springy in the holding direction 41 and as comparatively rigid transversely thereto. This is achieved, for example, via corresponding polar moments of inertia in conjunction with recesses 44, which can be recognized in FIGS. 5 and 6.

Finally, FIG. 7 shows another embodiment of the holding device 19, in which the coupling means 25 has at least one elastomer body 45 or at least one spring element 46. Basically, an embodiment, in which both at least one elastomer body 45 and at least one spring element 46 are provided, is also conceivable. Furthermore, the coupling means 25 here comprises a linear guide 47, which, in the example shown, is formed by a pin 48 and a bushing 49, in which the pin 48 is arranged in an adjustable manner bidirectionally. The linear guide 47 thus defines the holding direction 21 and stabilizes the coupling means 25 transversely to the holding direction 21. By contrast, the elastomer body 5 or the spring element 46 generates the elasticity of the coupling means 25 parallel to the holding direction 21. In the example of FIG. 7, the pin 48 is rigidly connected with the bracket 24, while the bushing 49 is rigidly connected with the vehicle structure 3.

According to the embodiments shown in FIGS. 1, 2 and 4, the actuator 2 is preferably held on the vehicle structure 3 exclusively via the holding devices 19. As a result, no holding forces can thus be transmitted to the housing 4 especially via the sound emission pipe 5. In the examples shown, the sound emission pipe 5 is arranged detached in the surrounding area 6 of the actuator 2, i.e., it has no contact with the other components of the vehicle.

While specific embodiments of the invention have been shown and described in detail to illustrate the application of the principles of the invention, it will be understood that the invention may be embodied otherwise without departing from such principles.

What is claimed is:

1. An electroacoustic actuator arrangement on a vehicle structure of a motor vehicle, the electroacoustic actuator arrangement comprising:

an actuator housing;

at least one loudspeaker which separates a front volume from a rear volume in the housing;

a sound emission pipe protruding outwards from the housing and fluidically coupled with the front volume;

a plurality of holding devices holding the actuator on the vehicle structure, the holding devices being arranged spaced apart from one another in a circumferential direction of the housing, each of the plurality of holding devices is springy in a holding direction and is rigid transversely to the holding direction, providing a reduced transmission of vibrations between the actuator and the vehicle structure.

2. An arrangement in accordance with claim 1, wherein the holding directions of the holding devices run parallel to one another.

3. An arrangement in accordance with claim 1, wherein the holding directions of the holding devices run parallel to an excitation direction of the loudspeaker, in which the loudspeaker transmits excitation forces to the housing during the operation of the actuator.

4. An arrangement in accordance with claim 1, wherein each of said holding devices comprises a bracket rigidly connected with the housing and a coupling, the bracket being connected with the vehicle structure springily and rigidly transversely thereto via the coupling in the holding direction.

5. An arrangement in accordance with claim 4, wherein at least one of the holding devices and the brackets define a holding plane, which extends vertically to an excitation direction of the loudspeaker.

6. An arrangement in accordance with claim 4, wherein at least one of the holding devices and the brackets are arranged at locations equidistantly to a force inlet point of the loudspeaker, from which locations the at least one of the holding devices and the brackets transmit excitation forces from the loudspeaker to the housing during the operation of the actuator.

7. An arrangement in accordance with claim 4, wherein at least one of the holding devices and the brackets are arranged equidistantly to a mass center of the actuator.

8. An arrangement in accordance with claim 1, wherein a mass center of the actuator and a force inlet point, from which the holding devices transmit excitation forces from the loudspeaker, during the operation of the actuator, to the housing, are essentially arranged in one another or above one another in the direction of gravity.

9. An arrangement in accordance with claim 1, wherein the loudspeaker is arranged in the housing such that an excitation direction of the loudspeaker, in which the loudspeaker transmits excitation forces to the housing during the operation of the actuator, runs parallel to the direction of gravity.

10. An arrangement in accordance with claim 4, wherein the respective coupling is designed as an elastomer bearing.

11. An arrangement in accordance with at least claim 10, wherein:

the elastomer bearing has a first elastomer area, which supports the bracket in the holding direction on the vehicle structure;

the elastomer bearing has a second elastomer area, which supports the bracket in the holding direction on a side facing away from the vehicle structure at a disk;

the disk is rigidly connected with the vehicle structure by means of a screw connection, which extends through the two elastomer areas and the bracket.

12. An arrangement in accordance with claim 4, wherein the respective coupling comprises an elastomer body, which is rigidly connected with the respective bracket, on the one hand, and is rigidly connected with a holder fastened to the vehicle structure, on the other hand, whereby the elastomer body is designed to be springy in the holding direction and rigid transversely thereto.

13. An arrangement in accordance with claim 4, wherein the coupling comprises at least one of at least one elastomer body and at least one spring element as well as at least one linear guide defining the holding direction.

14. An arrangement in accordance with claim 1, wherein:

the actuator is held on the vehicle structure exclusively via the holding devices; and the sound emission pipe is arranged detached in a surrounding area of the actuator.

15. An electroacoustic actuator arrangement for connection to a vehicle structure of a motor vehicle, the electroacoustic actuator arrangement comprising:

an actuator housing;

at least one loudspeaker which separates a front volume from a rear volume in the housing;

a sound emission pipe protruding outwards from the housing and fluidically coupled with the front volume; and a plurality of holding devices, each of the holding devices holding the actuator on the vehicle structure, the holding devices being arranged spaced apart from one another in a circumferential direction of the housing, each of the holding devices having a greater elasticity in the holding direction than in a direction transversely thereto, providing a reduced transmission of vibrations between the actuator and the vehicle structure.

16. An electroacoustic actuator arrangement and a motor vehicle comprising:

a vehicle structure of the motor vehicle;

an actuator housing;

at least one loudspeaker which separates a front volume from a rear volume in the housing;

a sound emission pipe protruding outwards from the housing and fluidically coupled with the front volume;

a plurality of holding devices holding the actuator on the vehicle structure, the holding devices being arranged spaced apart from one another in a circumferential direction of the housing, each of the plurality of holding devices is springy in a holding direction and is rigid transversely to the holding direction, providing a reduced transmission of vibrations between the actuator and the vehicle structure.

17. An arrangement and motor vehicle in accordance with claim 16, wherein the holding direction of each holding device runs essentially parallel to an excitation direction of the loudspeaker, in which the loudspeaker transmits excitation forces to the housing during the operation of the actuator.

18. An arrangement and motor vehicle in accordance with claim 16, wherein each holding device comprises a bracket rigidly connected with the housing and a coupling, the bracket being connected with the vehicle structure springily and rigidly transversely thereto via the coupling in the holding direction.

19. An arrangement and motor vehicle in accordance with claim 18, wherein at least one of the holding devices and the brackets are arranged at locations equidistantly to a force inlet point of the loudspeaker, from which locations the at least one of the holding devices and the brackets transmit excitation forces from the loudspeaker to the housing during the operation of the actuator.

20. An arrangement and motor vehicle in accordance with claim 18, wherein a mass center of the actuator and a force inlet point, from which the holding devices transmit excitation forces from the loudspeaker, during the operation of the actuator, to the housing, are essentially arranged in one another or above one another in the direction of gravity.

* * * * *